United States Patent [19]
Roller

[11] Patent Number: 5,127,897
[45] Date of Patent: Jul. 7, 1992

[54] THERAPEUTIC BACK SUPPORT DEVICE

[76] Inventor: Clare F. Roller, 353 W. Castle Rd., Fostoria, Mich. 48435

[21] Appl. No.: 630,547

[22] Filed: Dec. 20, 1990

[51] Int. Cl.$^5$ .............................................. A61F 5/01
[52] U.S. Cl. ..................................... 602/19; 602/16; 128/99.1; 128/107.1
[58] Field of Search ................... 128/78, 95.1, 99.1, 128/102.1, 104.1, 869, 870, 68, 69

[56] References Cited

U.S. PATENT DOCUMENTS

| | | | |
|---|---|---|---|
| 421,635 | 2/1890 | Teufel | 128/78 |
| 766,863 | 8/1904 | Adams | 128/78 |
| 2,029,557 | 2/1936 | Buckley | 128/104.1 |
| 2,146,444 | 5/1936 | Roe | 128/95.1 |
| 2,160,709 | 5/1939 | Peckham | 128/78 |
| 2,733,712 | 2/1956 | Wuesthoff | 128/78 |
| 2,871,850 | 2/1959 | Peckham | 128/78 |
| 3,532,090 | 10/1970 | Ward et al. | 128/95.1 |
| 3,889,664 | 6/1975 | Heuser et al. | 128/78 |
| 4,708,130 | 11/1987 | Grudem | 128/78 |

FOREIGN PATENT DOCUMENTS 583226  4/1931  Fed. Rep. of Germany ........ 128/78

Primary Examiner—Richard J. Apley
Assistant Examiner—Susan L. Weinhoffer
Attorney, Agent, or Firm—John J. Swartz

[57] ABSTRACT

A therapeutic back support device for use in applying force to vertically opposite sides of a human spine at any selected one of a plurality of different vertical levels. The device includes a back support plate which is coupled to a human body to forwardly direct the plate. A pair of force concentrating members are mounted on the front face of the plate between the plate and the body for concentrating the forwardly directed force of the plate to a specific portion of the back. The force concentrating members may be laterally and vertically moved to apply the force to any selected one of a plurality of vertically spaced spinal vertebrae.

16 Claims, 2 Drawing Sheets

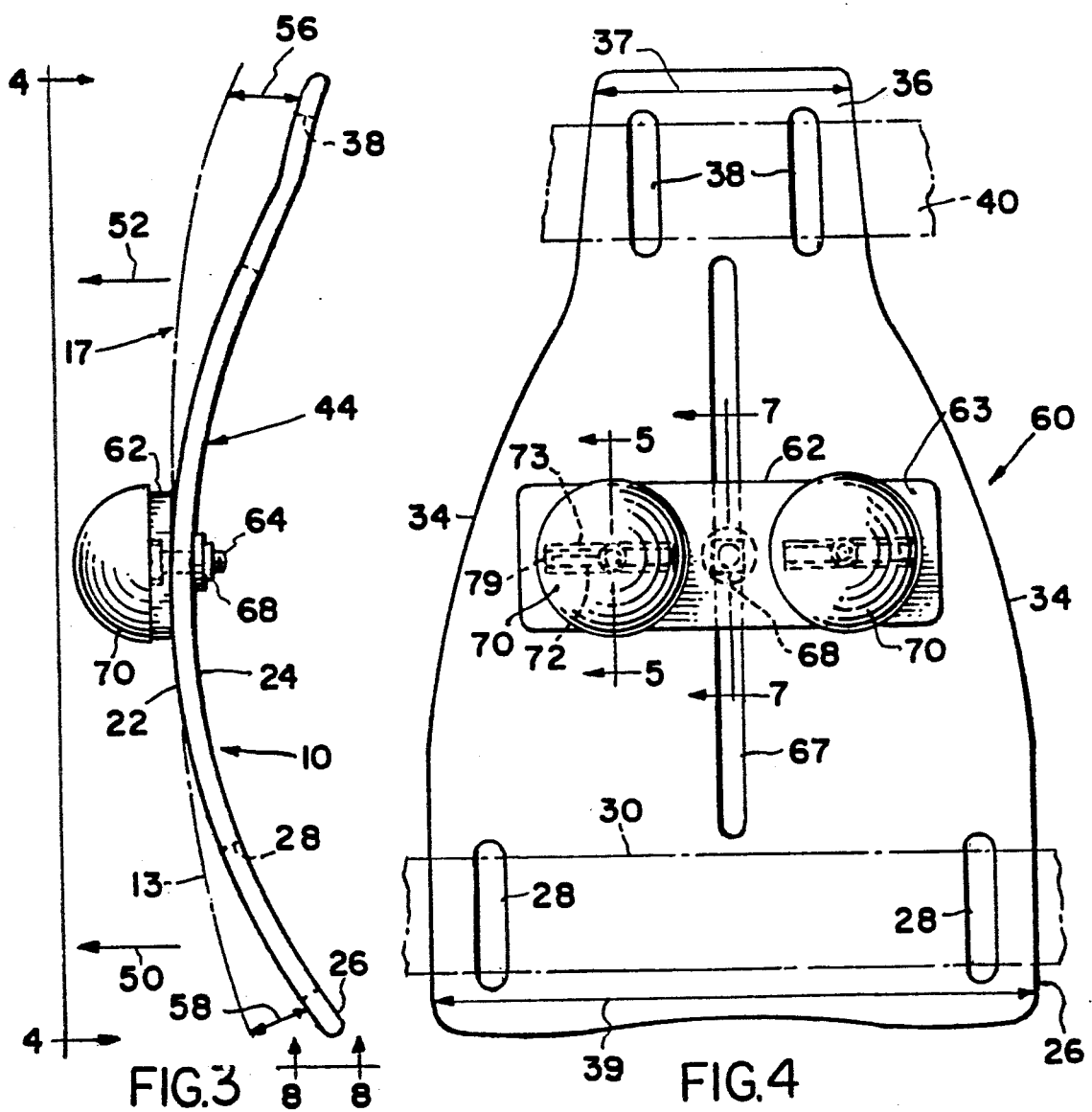
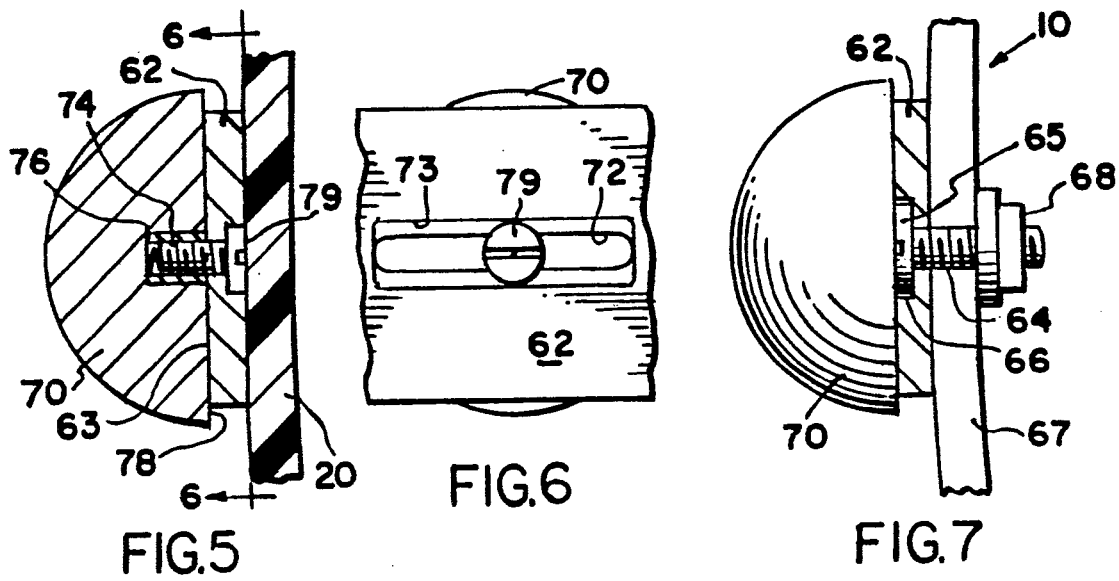

THERAPEUTIC BACK SUPPORT DEVICE

BACKGROUND OF THE INVENTION

1. Field of the Invention

This invention relates to a back support device and more particularly to a therapeutic back support device which can apply force and pressure to selected portions of the human spine.

2. Description of the Prior Art and Objects

Many individuals are afflicted with back problems at sometime during their lives. Various treatments and modalities have been utilized to treat back ailments.

Osteopathic physicians and chiropractors frequently manipulate a portion of the spine to remedy back ailments. Such manipulation sometimes includes the applying of force and pressure to specific localized areas.

It has been found advantageous to have such force directed at specific portions of the spine for periods of times which far exceed that normally associated with such manipulative therapy. It has also been found that effective treatment can include applying different amounts of pressure at different intervals, depending upon the stage of healing.

Accordingly, it is an object of the present invention to provide a therapeutic back support device of the type described which includes a back stabilizing support and mechanism for coupling the support to a human body to forwardly urge the back support toward the body and force concentrating members located between the support and body for localizing the forwardly transmitted force.

It is another object of the present invention to provide a back support device which can be mounted along the back of a human and includes mechanism for applying localized force to any selected one of a plurality of different portions of the human spine along the length of the spine.

It is another object of the present invention to provide a therapeutic back support device of the type described including a back support plate mounting force concentrating transmitting members on the forward face thereof for transmitting forces to laterally opposite sides of a human spine.

It is yet another object of the present invention to provide a therapeutic back support device of the type described including a back support plate and force transmitting members mounted on the forward face thereof and mechanism for mounting the force transmitting members in any selected one of a plurality of different vertically spaced positions along the length of a spine.

It has been found desirable to sometimes stabilize the spine, particularly the lumbar spine, with a stabilizing plate. It has been found, according to the present invention, that such stabilization can be more effective if the plate is curvilinear and includes a curvature greater than the normal curvature of a human spine.

Accordingly, it is an object of the present invention to provide a therapeutic back support of the type described including a back stabilizing curvilinear plate which has a curvature greater than the normal curvature of a human spine.

It is another object of the present invention to provide a therapeutic back support device of the type described including a curvilinear plate constructed of yieldable material which will allow the plate to straighten from its normally curved position to a less curved position and mechanism for attaching the plate to the human body to apply force thereto to straighten the plate.

Other objects and advantages of the present invention will become apparent to those of ordinary skill in the art as the description thereof proceeds.

SUMMARY OF THE INVENTION

A therapeutic back support device for treating a human spine comprising: a back stabilizing support plate, having front and rear faces, for positioning rearwardly adjacent a human body; mechanism for coupling the support plate to the human body to forwardly force the plate in a direction toward the spine; and force concentrating and transmitting members mounted on and projecting forwardly of the forward face of the plate for concentrating the forwardly directed force to a specific portion of the spine.

DESCRIPTION OF THE DRAWINGS

The invention may be more readily understood by referring to the accompanying drawings, in which:

FIG. 3 is an enlarged side elevational view illustrating the back support plate in a normal, relaxed position adjacent the back of a human body in an unstressed condition;

FIG. 4 is a front elevational view thereof taken along the line 4—4 of FIG. 3;

FIG. 5 is a further enlarged, fragmentary sectional end view taken along the line 5—5 of FIG. 4, more particularly illustrating force concentrating mechanism mounted on the forward side of the back support plate;

FIG. 6 is a further enlarged fragmentary view, taken along the line 6—6 of FIG. 5;

FIG. 7 is a further enlarged sectional end view, taken along the line 7—7 of FIG. 4.

DESCRIPTION OF THE PREFERRED EMBODIMENT

Figure 1:
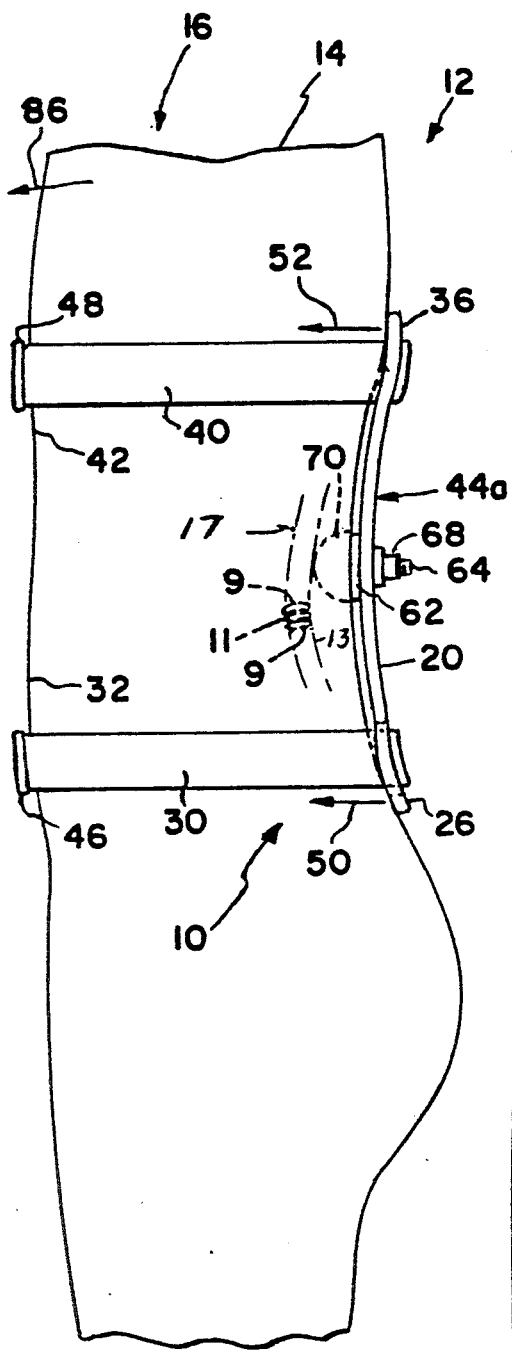
FIG. 1 is a side elevational view of apparatus constructed to the present invention mounted, in a stressed operative condition, on a human body.

Apparatus constructed according to the present invention, generally designated 10, is particularly adapted for mounting on the back 12 of a trunk 14 of a human body, generally designated 16. The human back 12 includes an upstanding spine 17 having a plurality of vertically stacked vertebrae schematically designated 9, separated by vertebral disks, schematically designated 11. The seven uppermost vertebrae 9 are commonly known as the cervical vertebrae and make up the cervical spine. The next lower 12 vertebrae are commonly known as the thoracic vertebrae and make up the thoracic spine. The next lower five vertebrae are commonly referred to as the lumbar vertebrae and make up the lumbar spine. The remaining portions of the spine is referred to as the sacrum. The lumbar spine includes a lordotic curvature 13, schematically illustrated in FIG. 1 and 3.

The therapeutic back support device 10 includes an upstanding curvilinear back support plate, generally designated 20, having a front face 22 and a rear face 24. The back support plate 20, includes a lower portion 26 having a pair of laterally spaced apart belt receiving slots 28 therein for receiving a lower belt 30 which is detachably coupled about the waist 32 of the user via a belt buckle 48.

Figure 2:
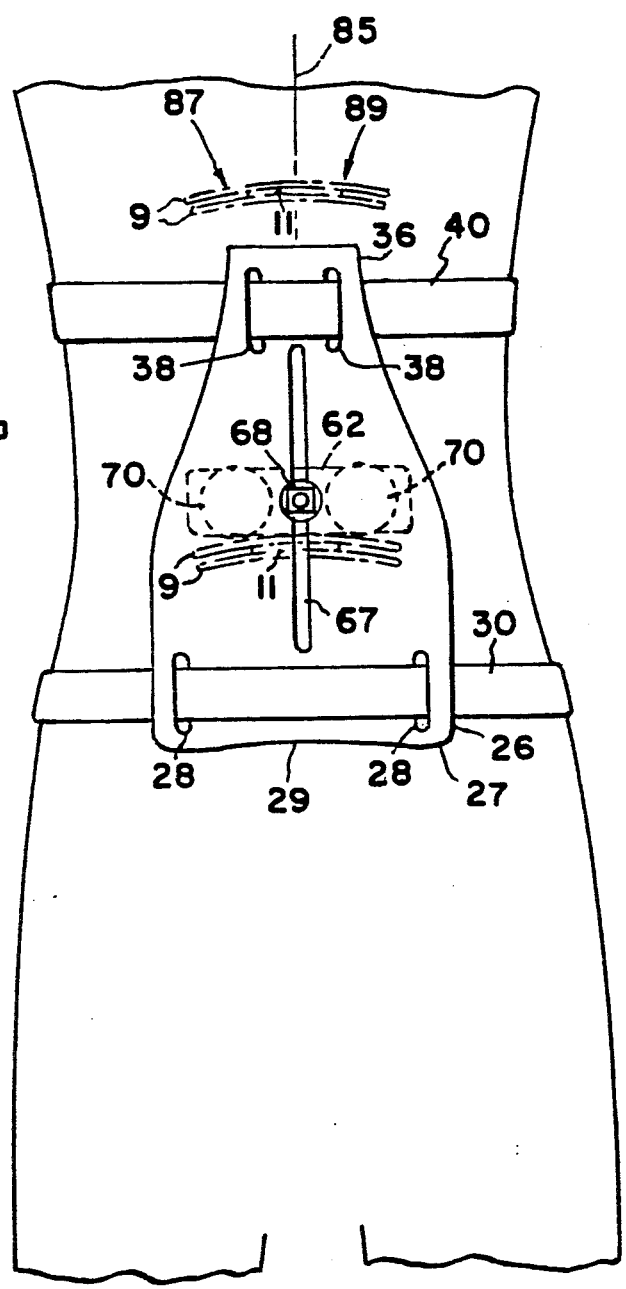
FIG. 2 is a rear elevational view thereof.

The side edge portions 34 of the plate 10 upwardly converge to an upper plate portion 36 which has a width 37 substantially less than the width 39 of the lower portion 26. The upper plate portion 36 includes a pair of laterally spaced apart slots 38 for receiving an upper belt 40 that is detachably coupled around the upper torso 42 of the body 16 via a belt buckle 48. The support 20 is constructed of firm, but yieldable, plastic material and is normally positioned as illustrated in FIG. 3 with a predetermined curvature represented by the arrow 44. The plastic material will tend to urge the plate 20 to the position illustrated in FIG. 3, but will yield to allow the plate 20 to be moved to a straightened, stressed position illustrated in FIGS. 1 and 2. The belt buckles or hasps 46 and 48 of belts 30 and 40, respectively, can be used to adjust the length of the belts 30 and 40, respectively, and thus adjust the forwardly directed force, represented by the arrows 50 and 52, to allow the plate 20 to move to any selected one of a plurality of different more straightened positions between the relaxed, unstresed position illustrated in FIG. 3 and the stressed operative position illustrated in FIG. 1.

As illustrated in the drawings, the normal radius of curvature 44 of plate 20 in the relaxed, unstressed condition is somewhat less than the normal radius of curvature 13 of the human spine, schematically designated 17. When positioned in the rest position as illustrated in FIG. 3, the upper plate portion 36 is spaced from the confronting vertebrae 9 by a distance 56 and the lower portion 26 is spaced from the confronting human vertebrae 9 by a distance 58. The belts 30 and 40 can be appropriately tightened to reduce that space and to increase the radius curvature of plate 20 to that illustrated at 44a in FIG. 1.

Mounted on the forward face 22 of the back support plate 20 is force concentrating and transmitting mechanism, generally designated 60. The force transmitting concentrating mechanism 60 includes a transversely extending pressure bar or slide 62 mounted for vertical movement on the plate 20 via a bolt if pin 64 having a head 65 mounted in a counter sunk hole 66 provided in the front face of the bar 62. The bolt 64 is slidably received in a vertical slot 67 centrally located in the plate 20 to allow the bar 62 to be vertically moved to a selected one of a plurality of different positions depending on which of the vertebra 9 is to be worked on. The bar 62 can be locked in any selected position by a nut 68 threadedly received on the bolt 64.

Mounted on the front face 63 of the bar 62 is a pair of semi-spherical, force transmitting and localizing members 70. A pair of elongate transverse slots 72 is provided on laterally opposite sides of the bar 62 64. A bolt 74 is received in each slot 72 and is detachably threadedly received in a ferrule 76 provided in the back side 78 of each of the semi-spherical force transmitting members 70. The elongate slots 72 are counter-sunk at 73 to receive the heads 79 of the bolts 74.

Figure 8:
FIG. 8 is a bottom plan view taken along the line 8—8 of FIG. 3 to particularly illustrate the curvature of the lower end portion of the back support plate.

As illustrated in FIG. 8, the lower portion 26 of the back support plate 10 is curved in a laterally outer direction such that the lateral lower edge portions 27 are normally positioned slightly forwardly of the central lower plate portion 29. The radius of curvature 84 of the lower plate portion 26 straightens from the unstressed position, illustrated in solid lines in FIG. 8, to the stressed position, illustrated in chain lines in FIG. 8, when the lower belt 30 is tightened and thus the lower edge mid plate portion 29 moves forwardly relative to said laterally spaced lower edge portions 27.

The semi-spherical force applying and transmitting members 70 are positioned on laterally opposite sides of the central vertical axis 85 of the spine 17 to apply force and pressure to laterally opposite sides 87 and 89 of the vertebrae 9. Of course, one of the members 70 may be removed if the practioner wants to apply force to only one lateral side of a vertebra 17.

THE OPERATION

The practitioner will normally position the back support plate 20 adjacent the lower lumbar spine of the patient in the position illustrated in FIG. 3. The treater will determine which of the patient's vertebrae 9 of the spine 17 or which portion of the lower back will require force and pressure applied thereto and will laterally adjust the semi-sperical members 70 on the bar 62 to an appropriate location by merely unthreading the semi-spherical member 70 from the bolts 74 and laterally moving the bolts and members 70 to an appropriate lateral location. The semi-spherical members 70 are then tightened onto the bolts 74 to fix them in position.

The treater will then also determine the appropriate vertical position of the semi-spherical member 70 and will adjust same by untightening the central bolt 64 and/or nut 68 and vertically positioning the pressure slide 62 and then retightening the bolt 64.

With the semi-spherical members properly positioned relative to the plate 20, device 10 re-positioned as illustrated in FIG. 3. The belts 30 and 40 are then tightened to straighten the plate 20 and urge the plate 20 forwardly towards the human body via the forces represented by the arrows 50, 52.

As the plate 10 is straightened, the forwardly directed force, represented by the arrows 50 and 52, will be transmitted to the semi-spherical members 70 which will apply point pressure to the selected portions of the lower portion of the spine 17. The amount of pressure applied can be adjusted by merely adjusting the length of the belts 30 and 40.

It is to be noted that if the patient tries to bend forwardly about the waist, the patient will tend to swing the body forwardly in the direction of the arrow 86 and the upper trunk 42 will swing forwardly further than the waist 32. Thus the upper belt 42 will apply substantially greater pressure to the upper back than the pressure applied by lower belt 30 to the lower back. This increased force of belt 42 will restrict forward swinging or bending movement of the user and such restriction will tend to immobilize the spine to preclude damage to the spine by inappropriate movements while the device is in position on the user.

If desired, rather than the lower belt 30, a user could merely slide the lower portion 26 underneath the upper waist portion of a pair of pants which the user would wear.

It is to be understood that the drawings and descriptive matter are in all cases to be interpreted as merely illustrative of the principles of the invention, rather than as limiting the same in any way, since it is contemplated that various changes may be made in various elements to achieve like results without departing from the spirit of the invention or the scope of the appended claims.

What I claim is:

1. A therapeutic back support device for treating a human spine located in a human back of a human body comprising:
   a support plate adapted to be positioned rearwardly adjacent said human back;
   said support plate being curvilinear and including upper and lower portions on vertically opposite ends of an intermediate portion;
   said support plate including a front face and a back face;
   said support plate having a normal predetermined radius of curvature in an unstressed position such that said upper and lower portions are rearward of said intermediate portion but being yieldable to allow said upper and lower portions to be moved forwardly relative to said intermediate portion to a stressed position to increase said radius of curvature;
   mount means coupled to said plate for encircling said body to forwardly move said upper and lower portions of said plate relative to said intermediate portion to force said intermediate portion into intimate engagement with said human back and move said upper and lower portions to any selected one of a plurality of different positions between said unstressed position and said stressed position; and
   force concentrating and transmitting means, mounted on and projecting forwardly of the front face of said plate, for engaging and transmitting force from said plate to selected portions of said human back including
      a pair of laterally spaced apart force transmitting members for applying forwardly directed force to laterally opposite sides of said human spine;
      a laterally disposed mounting bar mounting said force transmitting members on said plate for vertical movement to any selected one of a plurality of different vertically spaced positions; and
      means detachably mounting said force transmitting means on said bar for lateral movement relative thereto to any selected one of a plurality of different laterally spaced apart positions.

2. The therapeutic back support device set forth in claim 1 wherein said plate includes an elongate vertical slot;
   said means mounting said force transmitting means on said plate for vertical movement including pin means coupled to said support bar and received by said slot for vertical sliding movement therein, and means for detachably coupling said pin means to said plate in any selected one of a plurality of different vertically spaced positions.

3. The therapeutic back support device set forth in claim 2 wherein said mount means includes upper and lower belts coupled to said upper and lower portions, respectively, for passing around a portion of said human body.

4. The back support device set forth in claim 1 wherein said upper and lower portions include laterally spaced apart belt receiving means; said mount means includes upper and lower belts received by the said laterally spaced apart belt receiving means on said upper and lower portions, respectively of said plate.

5. The back support device set forth in claim 1 wherein said upper portion has a predetermined width and said lower portion has a substantially greater predetermined width.

6. The device set forth in claim 1 wherein said force transmitting means includes a pair of laterally spaced apart semi-spherical members.

7. The back support device set forth in claim 1 wherein said lower portion of said plate includes a mid portion and laterally outer edge portions on laterally opposite sides of said mid portion, said lower portion of said plate being curved so that said laterally outer edge portions are, in said unstressed position, disposed forwardly of said mid portion intermediate said laterally outer edge portions but are rearwradly moveable relative to said mid portion in said stressed position.

8. The back support device set forth in claim 7 wherein said mount means includes laterally spaced apart belt receiving openings in said laterally outer edge portions and a belt receiving by said openings.

9. A therapeutic back support device for treating a human spine located in a human back of a human body comprising:
   a support plate adapted to be positioned rearwardly adjacent said human back;
   said support plate being curvilinear and including upper and lower portions on vertically opposite ends of an intermediate portion;
   said support plate including a front face and a back face;
   said support plate having a normal predetermined radius of curvature in an unstressed position such that said upper and lower portions are rearward of said intermediate portion but being yieldable to allow said upper and lower portions to be moved forwardly relative to said intermediate portion to a stressed position to increase said radius of curvature;
   mount means coupled to said plate for encircling said body to forwardly move said upper and lower portions of said plate relative to said intermediate portion to force said intermediate portion into intimate engagement with said human back and move said upper and lower portions to any selected one of a plurality of different positions between said unstressed position and said stressed position; and
   force concentrating and transmitting means mounted on and projecting forwardly of the front face of said plate for engaging and transmitting force from said plate to selected portions of said human back including a pair of laterally spaced apart semispherical members.

10. A therapeutic back support device for treating a human spine located in a human back of a human body comprising:
    a support plate adapted to be positioned rearwardly adjacent said human back;
    said support plate being curvilinear and including upper and lower portions on vertically opposite ends of an intermediate portion;
    said support plate including a front face and a back face;
    said support plate having a normal predetermined radius of curvature in an unstressed position such that said upper and lower portions are rearward of said intermediate portion but being yieldable to allow said upper and lower portions to be moved forwardly relative to said intermediate portion to a stressed position to increase said radius of curvature;
    mount means coupled to said plate for encircling said body to forwardly move said upper and lower portions of said plate relative to said intermediate portion to force said intermediate portion into intimate engagement with said human back and move said upper and lower portions to any selected one of a plurality of different positions between said unstressed position and said stressed position; and force concentrating and transmitting means mounted on and projecting forwardly of the front face of said plate for engaging and transmitting force from said plate to any selected one of a plurality of vertically and horizontally spaced portions of said human back;

said force concentrating and transmitting means comprising a laterally extending pressure slide and a pair of laterally spaced apart, forwardly projecting members mounted on said pressure slide for lateral movement relative thereto.

11. The therapeutic back support device set froth in claim 10 wherein said force concentrating and transmitting means includes means mounting said pressure slide for vertical movement to any selected one of a plurality of different, vertically spaced positions.

12. The device set forth in claim 11 wherein said means mounting said pressure slide for vertical movement includes a vertical slot in said intermediate portion of said support plate, and a pin coupled to said slide and received by said slot.

13. A therapeutic back support device for treating a human spine located in a human back of a human body comprising:
  a support plate adapted to be positioned rearwardly adjacent said human back;
  said support plate being curvilinear and including upper and lower portions on vertically opposite ends of an intermediate portion;
  said lower portion including a mid portion and laterally outer edge portions on laterally opposite sides of said mid portion;
  said support plate including a front face and a back face;
  said support plate having a normal predetermined radius of curvature in an unstressed position such that said upper and lower portions are rearward of said intermediate portion but being yieldable to allow said upper and lower portions to be moved forwardly relative to said intermediate portion to a stressed position to increase said radius of curvature;
  said lower portion of said plate being curved so that said laterally outer edge portions thereof are, in said unstressed position, disposed forwardly of said mid portion but are rearwardly moveable relative to said mid portion in said stressed position.

14. A therapeutic back support device for treating a human spine comprising:
  back stabilizing support means having front and rear faces for positioning rearwardly adjacent a human spine for stabilizing a human spine;
  means for coupling said support means to a human body to forwardly force said support means in a direction toward said spine; and
  force concentrating and transmitting means mounted on and projecting forwardly of said front face of said support means for concentrating the forwardly directed force of said support means to a specific portion of said spine;
  said force transmitting and concentrating means including
    a pair of laterally spaced apart force concentrating members projecting forwardly of said support means;
    a support bar;
    means mounting said force concentrating members on said support bar for lateral movement relative thereto to any selected one of a plurality of different laterally spaced positions on laterally opposite sides of said spline; and
    means mounting said support bar on said support means for movement to any selected one of a plurality of different vertically spaced positions along the length of said spine.

15. The therapeutic back support device set froth in claim 14 wherein said force transmitting members comprise semi-spherically shaped bodies.

16. The therapeutic back support device set forth in claim 15 wherein said support means comprises a curvilinear plate having a radius of curvature less than the radius of curvature of said spine and being constructed of yieldable material which will allow said plate to yield, when said coupling means forwardly forces said support means toward said spline, to a position in which said curvature is increased.

* * * * *